United States Patent [19]

Carmen et al.

[11] Patent Number: 4,902,287
[45] Date of Patent: Feb. 20, 1990

[54] STERILIZABLE SYSTEM FOR BLOOD STORAGE

[75] Inventors: Raleigh A. Carmen, Concord; Chi-Yong Chong, San Francisco, both of Calif.

[73] Assignee: Miles Inc., Elkhart, Ind.

[21] Appl. No.: 100,647

[22] Filed: Sep. 24, 1987

[51] Int. Cl.⁴ .................................................. A61J 1/00
[52] U.S. Cl. ................................... 604/416; 604/403; 604/408; 435/2; 424/101; 206/221
[58] Field of Search ............... 604/403, 414, 416, 410, 604/408, 82, 84, 87, 88, 89, 90, 92; 435/2; 366/150, 163, 159; 206/219, 221; 424/101

[56] References Cited

U.S. PATENT DOCUMENTS

| | | | |
|---|---|---|---|
| 2,724,383 | 11/1955 | Lockhart | 604/88 |
| 2,893,547 | 7/1959 | Earl et al. | 206/219 |
| 3,001,525 | 9/1961 | Hendricks | 604/416 |
| 3,064,802 | 11/1962 | Jess et al. | 206/219 |
| 3,163,163 | 12/1964 | Wilburn | 206/221 |
| 3,351,058 | 11/1967 | Webb | 206/219 X |
| 3,874,384 | 4/1975 | Deindoerfer et al. | 435/2 X |
| 4,007,738 | 2/1977 | Voshino | 128/214 D |
| 4,132,594 | 1/1979 | Bank et al. | 604/405 X |
| 4,162,676 | 7/1979 | Talcott | 604/408 |
| 4,181,140 | 1/1980 | Bayham et al. | 128/214.2 |
| 4,435,179 | 3/1984 | Walker | 604/410 |
| 4,455,299 | 6/1984 | Grode | 435/2 X |
| 4,507,114 | 3/1985 | Bohman et al. | 206/219 X |
| 4,507,119 | 3/1985 | Spencer | 604/280 |
| 4,573,506 | 3/1986 | Paoletti | 604/416 X |
| 4,586,928 | 5/1986 | Barnes et al. | 604/408 |
| 4,589,879 | 5/1986 | Pearson | 604/416 X |
| 4,606,734 | 8/1986 | Larkin et al. | 604/414 X |
| 4,608,043 | 8/1986 | Larkin | 206/219 X |
| 4,630,727 | 12/1986 | Feriani et al. | 604/416 X |
| 4,731,053 | 3/1988 | Hoffman | 604/410 X |

OTHER PUBLICATIONS

WO84/01292, Grode, "Method and Container for Storing Platelets", 8/1983.

Primary Examiner—Carl D. Price
Attorney, Agent, or Firm—James A. Giblin

[57] ABSTRACT

An improved heat sterilizable blood bag system adapted for containing and mixing of different materials originally placed in separate but potentially communicating compartments. The improvement comprises of having a smaller squeezable compartment for one material attached to and capable of communicating with a larger compartment for the other material. The material in the smaller compartment is separated from the interior of the larger compartment by means of an externally manipulatable closure means which, when opened, permits mixture of the contents in the first compartment and contents of the second compartment when the smaller compartment is repeatedly squeezed.

8 Claims, 1 Drawing Sheet

U.S. Patent
Feb. 20, 1990
4,902,287
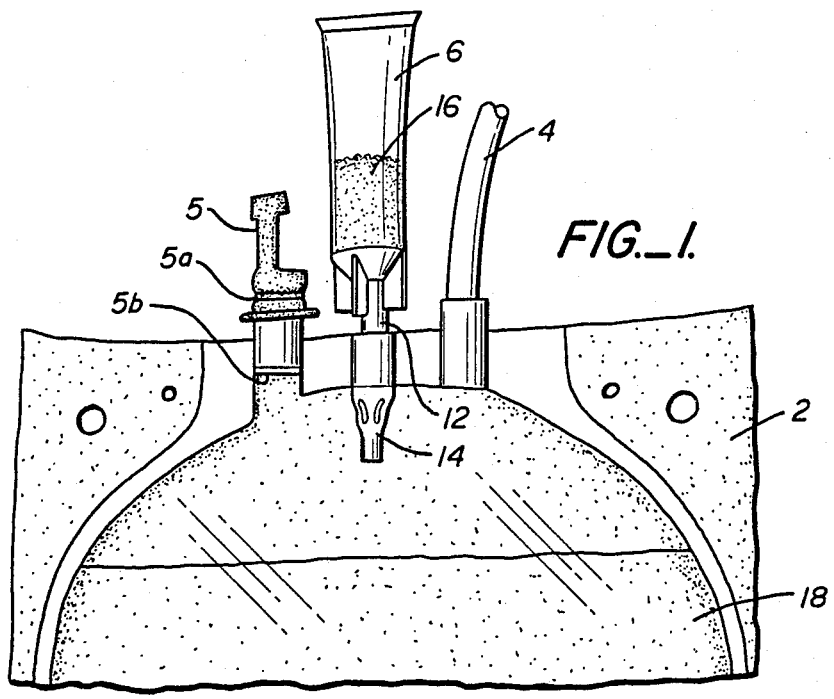
FIG._1.
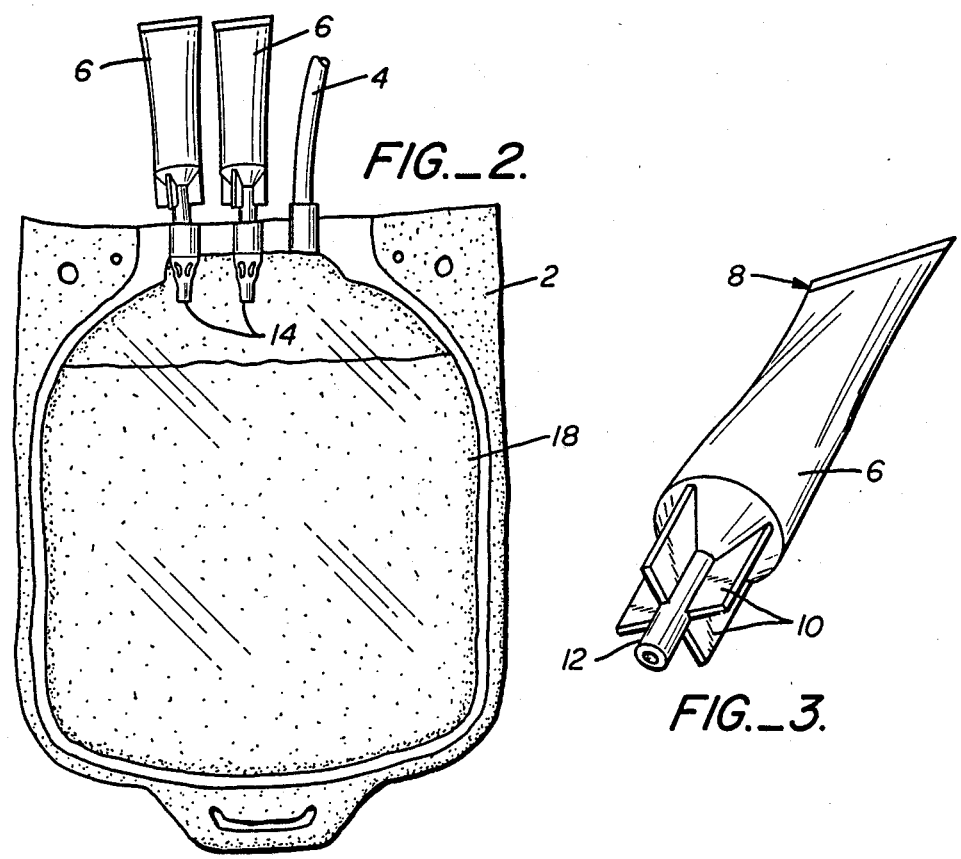
FIG._2.
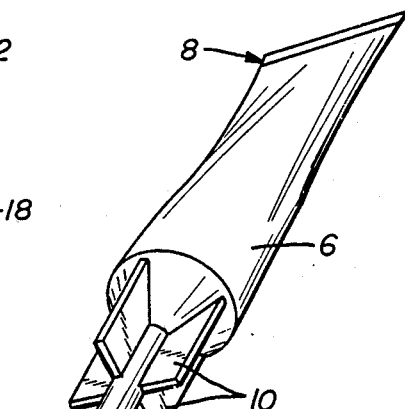
FIG._3.

STERILIZABLE SYSTEM FOR BLOOD STORAGE

BACKGROUND OF THE INVENTION

Field: This disclosure is concerned generally with blood preservation and especially with addition of agents for extended storage or treatment of blood components such as platelets and erythrocytes.

Prior Art: Blood Bag systems designed for the "closed" mixing of different materials such as liquid and solid components are known. See, for example, U.S. Pat. No. 4,484,920 to Kaufman et al showing a system for the flow-through mixing of liquid and solid components. The system disclosed in that patent is designed primarily for the mixing of solid drugs in a diluent. The disclosed mixing system uses an internal compartment containing a solid material (e.g., a drug). The compartment has two access ports, one at each end. These ports permit a diluent to pass through the compartment and carry with it the solid for ultimate mixing in a final larger container. The system of the patent does not appear to be concerned with the preservation and long term storage of blood components or the sterilization of such systems. Instead, the patent appears to be concerned with the reconstitution of lyophilized drugs, especially those that are difficult to reconstitute into solutions.

U.S. Pat. No. 4,162,676 to Talcott discloses the use of a $Ca(OH)_2$-impregnated silicone insert within a blood bag to control pH. However, it is not clear whether that system could successfully withstand heat sterilization temperatures and provide a controlled amount of the buffer.

It is well known that the storage of certain blood components in plastic bags can be enhanced by providing certain chemicals in the storage solution. For example, the control of pH of platelet concentrates is critical to long term storage and the pH can be controlled with certain buffers such as bicarbonate salts in solution. See also, U.S. Pat. No. 3,874,384 to Deindoerfer et al. and U.S Pat. No. 4,162,676 to Talcott, cited above. Ideally, such compounds should be available in a "closed" blood bag storage system. In such a system, the collection of blood, its separation into various components, its storage, and ultimate infusion of a given component into a patient, occurs without opening the system to the possibility of outside contaminants. This can be accomplished using pre-connected multiple blood bags (connected by tubings) having externally manipulated valves, etc. Unfortunately, some materials or compounds that would be useful for the storage of blood components can not be sterilized while in solution without degradation. Hence, they must be added as outside agents to an originally closed system after heat sterilization, thus causing the system to be "open" or have an increased chance of contamination.

We have now found that a closed but sterilizable blood bag storage system can be made to include chemicals that would degrade if mixed with other materials or in aqueous solution under heat sterilizing conditions. Details of our system are disclosed below.

SUMMARY OF THE INVENTION

The heat sterilizable blood bag system of this disclosure comprises a first, flexible plastic compartment attached to an edge an capable of communicating with a second, flexible plastic compartment such as a conventional blood bag. The first compartment is smaller, squeezable and adapted to contain a material such as a solid which can be subjected to sterilization conditions without substantial degradation. The second compartment is larger and adapted to contain a second material such as a liquid which serves as an aqueous diluent for the solid. Between the compartments, and within the system, is an externally manipulable closure means which, when opened by external manipulation, permits the material of the first compartment, upon squeezing of the first compartment, to mix with the material of the second compartment after the entire system has been sterilized. By being squeezable, the first compartment permits material (e.g. a liquid) from the second compartment to be drawn into the first compartment to initiate the mixing process. The bag system and its various components may be made of conventional and sterilizable plastics known to those skilled in the art.

BRIEF DESCRIPTION OF THE FIGURES

FIG. 1 is a partial plan view of a blood bag having a single, squeezable, and smaller chemical compartment of the type disclosed herein.

FIG. 2 is a plan view of a blood bag having a first smaller chemical compartment and a second smaller compartment which may contain additional dry chemical(s) or a liquid to be mixed with the contents in the larger bag.

FIG. 3 is a perspective view of the squeezable, smaller chemical compartment of FIGS. 1 and 2.

SPECIFIC EMBODIMENTS

As used herein, the term "closed" refers to a blood collection system with which blood or blood components may be collected, stored, processed or transferred within the system without the need to enter the system in a manner that results in the risk of contamination of the system from outside sources (other than the initial collection of blood from a donor). Such a closed system may comprise a single blood bag or a multiple blood bag system (i.e., a double, triple or "quad") comprising two or more blood bags pre-connected by tubings. The movement of various components within such a closed system may be controlled using known valving means such as external clamps for the tubings or, more preferably, externally manipulatable internal valves such as the so-called frangible valves (e.g., U.S. Pat. No. 4,586,928 to Barnes et al.) A closed system is meant to include initially connected blood bag system components (pre-connected) or a final system in which components have been subsequently connected using "sterile docking" devices of the type shown, for example, in U.S. Pat. No. 4,507,119.

Sterilizable means the capability of being subjected to temperatures of at least about 114° C. for at least about 30 minutes (or exposed to at least about 2.5 megarads of gamma radiation) without significant degradation of a given product. In the case of the dry or liquid compounds, chemicals or components of this disclosure, this means that such compounds, chemicals or components must retain at least 75 percent by weight of their initial pre-sterilization chemical identity and utility after having been subjected to the above sterilization conditions.

The closed, sterilizable system of this disclosure is illustrated in FIG. 1. That Figure shows the top portion of a storage bag 2 which is part of and connected via tubing to a closed multiple blood bag system via tubing 4. Tubing 4 may be connected directly to a blood donor collection bag (donor bag) or a satellite bag both of which are not shown. Alternatively, bag 2 may be a donor bag and tubing 4 may be connected directly to a donor needle for phlebotomy use.

Aqueous solution 18 may be an anticoagulant or blood component preservation solution or a blood component already in an aqueous solution.

Closure 5 is representative of a typical pull-off rubber seal which, when pulled off by tearing scored portion 5a, allows sterile access to the interior of bag 2, commonly after penetration of transverse membrane 5b.

Connected to bag 2 via conduit 12 is smaller compartment 6 which contains a pre-determined amount of a material which is not readily sterilizable in an aqueous solution such as 18. In FIG. 1, the compound 16 is preferably separated from liquid 18 by means of an externally manipulated frangible valve means like that shown in U.S. Pat. No. 4,586,928 to Barnes et al. Because of the proximity of smaller compartment 6 to bag 2, and the need to initiate mixture of the separate materials by repeatedly squeezing compartment 6, it is preferable to have a valving means 14 located outside of conduit 12. This is in distinction of other frangible valves that are physically located within such bag-connecting conduits. See, for example, U.S. Pat. Nos. 4,007,738 and 4,181,140.

It is important to the overall mixing process and use of this invention that smaller compartment 6 be squeezable. As used herein, squeezable means that the smaller compartment must be made of a resilient material (preferably a transparent plastic such as plasticized PVC) the construction of which forces the compartment to tend to return to its original shape after it has been deformed by external pressure (e.g., manual) on the compartment walls. Squeezability permits the smaller compartment to draw material from the larger compartment as the smaller compartment tends to return to its original shape after squeezing. Preferably, bag 2 is inverted during this squeezing (mixing) step so that the contents of the larger compartment immediately enters the smaller compartment through opened valve means.

By repeatedly squeezing compartment 6 after valve means 14 is opened and bag 2 inverted, thorough mixing of compound 16 with liquid 18 is assured. After the mixing is completed and chemical or compound 6 is thoroughly dissolved in liquid 18, compartment 6 may be drained by simply holding the system with compartment 6 above bag 2 and gently squeezing compartment 16. Compartment 6 can then optimally be removed after sealing at conduit 12. Alternatively, because of its relatively small internal volume (less than 5 ml.), compartment 6 may be left in place for the remainder of the bag's useful life. This alternative is preferable since it lessens the chance of outside contamination that could occur if compartment 16 were removed.

FIG. 2 illustrates a bag similar to that of Figure except that two smaller and squeezable compartments are shown in potential communication with the larger bag 2 after valve means 14 are opened. In FIG. 2, compartment 6 may contain the same or different compounds or chemicals and one of the compartments may even contain a liquid which is desirably mixed with the contents of bag 2 at a later time.

FIG. 3 shows a preferred squeezable compartment adapted to be attached to a part in a blood bag at conduit 12 via known means such as solvent welding or a combination of solvent welding and friction fit. As can be seen, compartment 6 is made to assure squeezability (as defined herein) by having two ends, the designs of which assure squeezability. Compartments 6 terminates at one end in a linear seal line 8 and terminates at the other end with vanes 10 which are designed to avoid any chance of a linear seal when pressure is put on compartment 6 walls by squeezing. Vanes 10 assure that when compartment 6 is squeezed, it will return to its original shape, thereby creating the partial vacuum in Conduit 12 needed to draw in the liquid for mixing with the solid (or perhaps other liquid) in compartment 6 prior to opening valve means 14. In addition, when compartment 6 is squeezed, especially repeatedly, the vanes 10 help assure that fluid already in compartment 6 will be forced through conduit 12 into bag 2 in jet-like fashion. In looking at FIG. 3, it is clear that the ends of squeezable compartment 6 must include a means for avoiding deformation of compartment 6 (such as the Vanes 10) which strengthen compartment 6 against deformation at one end. In this example, that is accomplished by forcing that end to be essentially cylindrical.

In the Example below, a bag similar to that shown in FIG. 1 (but without a liquid in bag 2) were subjected to sterilizing conditions with about 60 mg of sodium bicarbonate within compartment 6. The plastic film used to make the bag is described in U.S. Pat. No. 4,280,497, incorporated herein by reference. Also incorporated by reference into this application is PCT patent application WO 84/01292 filed in the name of G. Grode. That application describes the relationship of plastic film thickness, plasticizer type and plasticizer amount in controlling the pH of platelet storage bags. The results obtained after sterilization are described below. Although the Example is concerned with the effects of heat sterilization on sodium bicarbonate in dry form, it can be appreciated that any such heat sensitive solid or liquid material (e.g., drugs, etc.) may be contained in compartment 6, depending on the blood component to be stored in the main bag. Likewise, any aqueous solution (e.g., red blood cell preservation systems, anticoagulants, platelet storage solutions, etc.) that can withstand sterilization conditions may be in the main bag.

EXAMPLE

As noted earlier, platelet viability is irreversibly lost if pH falls to 6.0 or below. Sodium bicarbonate can control pH during platelet storage but due to instability during autoclaving cannot be employed in current liquid preservation systems. Sodium bicarbonate in aqueous state begins to break up into carbon dioxide and sodium carbonate at about 20° C. and completely on boiling. The test system was a system like that of FIG. 1 which included 60 mg of sodium bicarbonate in the smaller compartment 6. The system was then heat sterilized and the sodium bicarbonate was then mixed with a solution of platelet concentrates.

Eight platelet concentrates (PC) that had been stored for 5 days were used to test the disclosed system. All PC had good discoid morphology as judged by "streaming" appearance (Fratantoni et al, J. Lab. Clin. Med, 103:620, 1984). Four pools of 2 PC each were made, and sampled for measurement of pH and platelet count. One-half of each pool was transferred to a test bag containing the dry chemical pack with 60 mg of autoclaved $NaHCO_3$ and the other half was transferred to a control bag. After adding the dry chemical to the test PC, both test and control bags were returned to storage and tested at day 10. Results are given in the table below.

TABLE

| | Day 5 | | | Day 10 | |
|---|---|---|---|---|---|
| Pool | pH | Platelets, No/μL | Unit | pH | Streaming Category* |
| 1 | 7.03 | 1,164,000 | T1 | 7.33 | 2 |
| 2 | 7.06 | 1,612,000 | C1 | 7.01 | 1-2 |
| 3 | 7.21 | 1,520,000 | T2 | 7.14 | 1-2 |
| 4 | 7.19 | 1,388,000 | C2 | 6.36 | 0 |
| | | | T3 | 7.05 | 1-2 |
| | | | C3 | 6.45 | 0 |
| | | | T4 | 7.35 | 2-3 |
| | | | C4 | 6.96 | 2 |

*4 = best, 0 = worst

All test units had pH above 7.0 (mean 7.22) and reasonably good discoid morphology. Two control units had pH below 6.5 and very poor morphology.

Given the above disclosures, it is thought variations will occur to those skilled in the art. Accordingly, it is intended that the above examples should be construed as illustrative only and that the invention disclosed should be limited only by the following claims.

We claim:

1. In a closed, heat sterilizable, blood bag system comprising at least one flexible bag adapted to receive and store a blood component, the improvement comprising a squeezable, resilient compartment extending from the bag via a conduit and containing a solid, pH buffering material within the compartment, the solid material being separated from the interior of the flexible bag by means of an externally manipulable closure system located outside of the conduit which, when opened, permits the mixture of the solid pH buffering material with the contents of the bag, thereby assuring pH control of the bag contents over prolonged periods of time, the squeezable, resilient compartment providing means for drawing the contents of the flexible bag into the compartment when the closure system is opened.

2. The system of claim 1 wherein the solid pH control material comprises sodium bicarbonate.

3. The system of claim 2 wherein the sodium bicarbonate is in the form of a powder or tablet.

4. The system of claim 1 wherein the closure system comprises frangible valve.

5. In a method of storing platelets comprising holding platelets in a closed, flexible, gas permeable plastic bag for a given period, the improvement which comprises having attached to the bag a separate squeezable compartment which includes a heat sterilizable, solid pH buffering material, the buffering material being separated from the interior by means of an externally manipulatable closure system, the closure system capable of being manipulated to open communication between the interior of the bag and the interior of the compartment such that the contents of the bag and the compartment can be mixed for pH control of the bag contents.

6. The method of claim 5 wherein the pH buffering material comprises a bicarbonate salt, the amount of which is capable of maintaining the pH of a unit of platelets within the range of 6.8 to 7.4 for at least about 10 days.

7. The method of claim 6 wherein the buffering material is sodium bicarbonate in the form of a powder or a compressed tablet.

8. The method of claim 5 wherein the bag is made from a plastic film having a film thickness, plasticizer type and plasticizer content which, together, assure a gas transmissibility which facilitates long term storage of the platelets.

* * * * *